United States Patent [19]

Combourieu et al.

[11] Patent Number: 4,555,514
[45] Date of Patent: Nov. 26, 1985

[54] 3-ALKOXY-2-(N-PYROLIDINO)-N-PYRIDYL-N-FURYL(OR THIENYL) METHYL-PYROPYL AMINES USEFUL AS CALCIUM ANTAGONISTS

[75] Inventors: Michel Combourieu, Aurillac; Jacques A. L. Simond, Les Martres De Veyre; André J. Monteil, Chatel Guyon, all of France

[73] Assignee: Riom Laboratoires C.E.R.M. "RL-CERM" S.A., Riom, France

[21] Appl. No.: 690,051

[22] Filed: Jan. 9, 1985

[30] Foreign Application Priority Data

Jan. 18, 1984 [FR] France .................. 84 00755

[51] Int. Cl.⁴ .......................................... C07D 487/12
[52] U.S. Cl. ................................... 514/343; 546/281; 546/280
[58] Field of Search ............... 546/208, 209, 281, 280; 514/343

[56] References Cited

U.S. PATENT DOCUMENTS 4,463,005 7/1984 Jones et al. .................. 546/281

FOREIGN PATENT DOCUMENTS 1595031 8/1981 United Kingdom .

OTHER PUBLICATIONS

Morrison and Boyd, *Organic Chemistry*, 3d Edition, pp. 734–735 and 742.
Medicinal Chemistry, Third Edition, Part I, (Edited by Alfred Burger) pp. 74–77.

*Primary Examiner*—Henry R. Jiles
*Assistant Examiner*—P. Ann Bucci
*Attorney, Agent, or Firm*—Wegner & Bretschneider

[57] ABSTRACT

The present invention relates to new compounds of the general formula:

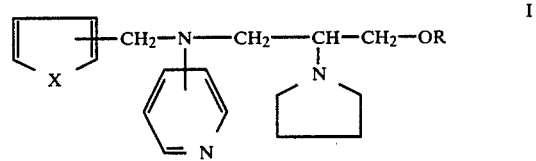

in which X represents oxygen or sulphur and
R represents a linear or branched alkyl group with 1 to 7 carbon atoms,
and pharmaceutically acceptable acid addition salts thereof, having valuable cardiovascular properties.

5 Claims, No Drawings

3-ALKOXY-2-(N-PYROLIDINO)-N-PYRIDYL-N-FURYL(OR THIENYL) METHYL-PYROPYL AMINES USEFUL AS CALCIUM ANTAGONISTS

The present invention relates to new 3-alkoxy-2-(N-pyrrolidino)-N-pyridyl-N-furylmethylpropyl amines and corresponding N-thienylmethyl analogs, to methods for their preparation and to a pharmaceutical composition containing same.

More particularly the compounds correspond to the following general formula:

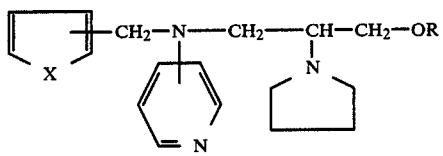

in which X represents oxygen or sulphur and
R represents a linear or branched alkyl group with 1 to 7 carbon atoms,
and pharmaceutically acceptable acid addition salts thereof.

The compounds of the invention possess valuable cardiovascular properties and more particularly they exert potent anti-anginal, anti-hypertensive and anti-dysrythmic activities.

The compounds of formula I may be prepared by methods known for the preparation of analogous compounds.

The compounds I may be prepared by the reaction of the compound of the formula II:

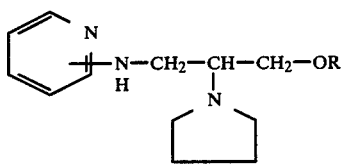

with a compound of the formula III

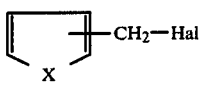

wherein R and X have the meanings assigned before and Hal represents halogen, and preferably chlorine and bromine.

The starting compound of formula II may, for example, be prepared by a reaction of a compound of the formula IV:

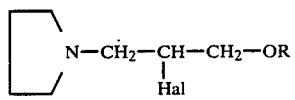

in which Hal and R have the meanings assigned above, with aminopyridine. This reaction is preferably carried out by first treating the appropriate aminopyridine with an alkalimetal-metallizing agent such as sodiumhydride or sodiumamide.

Another method for the preparation of the compounds of formula I consists of the reaction of a compound of the formula IV with a compound of the formula V:

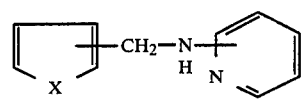

in which X has the meanings given before.

Preferably this reaction of compound IV with compound V is promoted by first metallizing the latter with an alkalimetal-metallizing agent, such as sodiumhydride or sodium, potassium or lithiumamide.

The compound of formula V may be obtained by a reaction of the aldehyde furaldehyde or the corresponding sulphur analog thereof with aminopyridine resulting in an imine, which imine may subsequently be reduced in situ to give the desired secondary amine of formula V. A suitable reducing agent, for example, is sodiumborohydride.

The compounds of general formula I and acid addition salts thereof were shown to possess valuable calcium antagonism properties demonstrated in vitro by usual pharmacological methods, see VAN ROSSUM, Arch. Int. Pharmacodyn. Ther. 143, 299–330 (1963).

In vivo, the anti-anginal activity was investigated by measuring the usual haemodynamic parameters (percentage variation and duration of action) on anaesthetized dogs:

Cardiac frequency with the aid of subcutaneous ECG electrodes.

Coronary arterial output with the aid of an electromagnetic flowmeter.

Anti-tachycardia action (inhibition of the positive chronotropic effects of isoprenaline).

The compounds of the invention are administered intravenously at a dose of 5 mg.kg$^{-1}$ and the results are reported in Table I.

TABLE I

| | | Compound EXAMPLE 1 | Compound EXAMPLE 2 |
|---|---|---|---|
| Cardiac frequency | Variation % | −19% | −22% |
| | Duration (min.) | >45 mn | >45 mn |
| Coronary output | Variation % | +97% | +65% |
| | Duration (min.) | 5 mn | 5 mn |
| Antitachycardia action | Variation % | −63% | −63% |
| | Duration (min.) | 45 mn | 45 mn |

The haemodynamic results recorded show that the compounds of the invention have substantial bradycardia and anti-tachycardia properties. In addition the compounds tested possess an appreciable coronary dilating effect.

The compounds of the invention were also shown to possess a low toxicity; their acute toxicity on oral administration to mice is generally greater than 500 mg.kg$^{-1}$.

The pharmacological properties therefore make it possible to use the compounds of the invention as drugs for the treatment of cardiovascular disorders such as angina pectoris, hypertension or rhythm disorders.

In association with the usual pharmaceutical excipients, they can be administered enterally or parenterally, preferably by the oral or intravenous route, at daily doses of between 1 and 15 mg per kg of body weight.

For the treatment of humans a daily dosage of between 40 and 1200 and more preferably between 100 and 800 mg may be used.

Mixed with suitable auxiliaries the compounds I or a salt thereof may be compressed into solid dosage units such as pills, tablets etc., or may be processed into capsules. By means of suitable liquids the compounds may also be applied as an injection- or oral-preparation in the form of solutions, suspensions or emulsions.

The compounds of formula I possess a chiral carbon, as a result of which a racemic mixture I and separate optical enantiomers I are possible. Both the racemic mixture, as well as the separate optical enantiomers belong to the compounds according to the invention. The separate optical enantiomers can be prepared in the usual manner by resolution of the racemic mixture or directly using optically active starting products.

The invention also encompasses the pharmaceutically acceptable acid addition salts of the compounds of formula I. These salts are usually obtained by combining the free base I with inorganic or organic acids such as hydrochloric acid, fumaric acid, maleic acid, citric acid or succinic acid, these acids being mentioned by way of illustration but without implying any limitation.

The alkyl group in the definition of R is a linear or branched alkyl group with 1 to 7 carbon atoms, such as methyl, ethyl, propyl, butyl, isobutyl, pentyl, isopentyl and hexyl. The isobutyl radical is the preferred group in the definition of R.

The group

includes all pyridyl radicals, whereby the 2-pyridyl radical is to be preferred.

The furyl and thienyl groups in the compounds according to the general formula I include the 2-furyl, 3-furyl, 2-thienyl and 3-thienyl radicals. The 2-furyl and especially the 2-thienyl radicals are to be preferred.

Preferred compounds according to the invention are the compounds of formula I and acid addition salts thereof in which—whether or not in combination—:

R represents the isobutyl moiety, the group

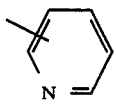

represents a 2-pyridyl moiety and the group

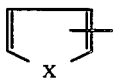

represents a 2-furyl or 2-thienyl moiety.

EXAMPLE 1

3-iso butoxy-2-pyrrolidino-N-(pyridin-2-yl)-N-(thien-2-yl methyl)propylamine

1. A mixture of 20 g (0.21 mol) of 2-aminopyridine in 400 ml of toluene, and 7.5 g (0.25 mol) of 80% NaH was heated under reflux for ½ hour. After the mixture had been allowed to return to ambient temperature, 46.15 g (0.21 mol) of 2-chloro-1-isobutoxy-3-pyrrolidinopropane were added and the mixture was refluxed for 3 hours. After cooling down to ambient temperature, the mixture was washed with water, dried over MgSO₄ and filtered, the solvent was evaporated and the residue was distilled under reduced pressure.

This gave 38.8 g of 3-isobutoxy-2-pyrrolidino-N-(pyridin-2-yl)propylamine having a boiling point of b.p. 0.05=154° C.

2. A mixture of 14 g (0.053 mol) of the above amine in 250 ml of toluene and 2 g (0.067 mol) of NaH was heated under reflux for ½ hour, After which 7.3 g (0.055 mol) of 2-chloromethyl-thiophene were added and the mixture was refluxed again for 3 hours. After cooling down the mixture was washed with water, dried over MgSO₄ and filtered, whereupon the solvent was evaporated and the residue distilled under reduced pressure.

This gave 4 g of the title compound having a boiling point: b.p. 0.05=180° C. Melting point of the hemifumarate salt: 99.8° C.

EXAMPLE 2

3-isobutoxy-2-pyrrolidino-N-(pyridin-2-yl)-N-(furfuryl)-propylamine

1. A mixture of 20 g (0.213 mol) of 2-aminopyridine and 22.5 g (0.234 mol) of furfural in 400 ml of benzene was refluxed for 2 hours. The benzene was then evaporated off and the residue was taken up with 500 ml of methanol. The mixture was stirred in an ice bath whereupon 8.9 g (0.234 mol) of NaBH₄ were added in small portions. The mixture was then stirred at ambient temperature for 5 hours. After the methanol had been evaporated off, the residue was extracted with ether to give 24.1 g of furfuryl aminopyridine having a boiling point of b.p. 0.1=98° C.

2. A mixture of 12 g (0.068 mol) of the above amine in 200 ml of toluene and 2.8 g (0.092 mol) of 80% NaH was then heated under reflux for ½ hour and allowed to return to ambient temperature. 14.9 (0.068 mol) of 2-chloro-1-isobutoxy-3-pyrrolidinopropane were then introduced and the mixture was heated under reflux. The excess NaH was then destroyed with a small quantity of water saturated with NaCl, whereupon the mixture was washed with water, dried over MgSO₄ and filtered. Toluene was evaporated off and the residue was distilled under reduced pressure. This gave 8.6 g of the title compound having a boiling point of b.p. 0.05=169° C.

We claim:

1. A compound of the general formula:

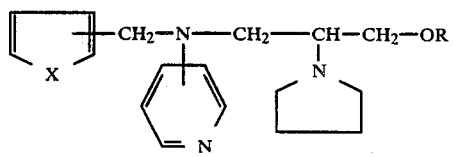

in which X represents oxygen or sulphur and

R represents a linear or branched alkyl group with 1 to 7 carbon atoms, or a pharmaceutically acceptable acid addition salt thereof.

2. A compound according to claim 1, characterized in that R represents the isobutyl radical.

3. A compound according to claim 1, characterized in that the group

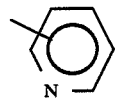

represents the 2-pyridyl group.

4. A compound according to claim 1, characterized in that the group

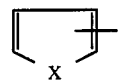

represents the 2-thienyl group.

5. A calcium antagonistic composition comprising a calcium antagonistic effective amount of a compound of claim 1 and a pharmaceutically acceptable excipient therefor.

* * * * *